US00PP09609P

United States Patent [19]

Meilland

[11] Patent Number: Plant 9,609

[45] Date of Patent: Jul. 23, 1996

[54] HYBRID TEA ROSE PLANT NAMED 'MEIBRINPAY'

[75] Inventor: Alain A. Meilland, Antibes, France

[73] Assignee: The Conard-Pyle Company, West Grove, Pa.

[21] Appl. No.: 491,716

[22] Filed: Jun. 19, 1995

[51] Int. Cl.[6] ..... A01H 5/00

[52] U.S. Cl. ..... Plt./16

[58] Field of Search ..... Plt./15, 16, 24, Plt./25

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms on a substantially continuous basis light orange blossoms. Such blossoms are long-lasting and are similar in configuration to old-fashioned roses. The plant exhibits a narrow and bushy growth habit and strong vegetation. The new variety exhibits very good disease resistance and is particularly well suited for use as attractive ornamentation in the landscape.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Just Joey' variety (non-patented in the United States). The male parent (i.e., the pollen parent) was formed by the cross of the 'Meirestif' variety (non-patented in the United States) and the 'Meinarval' variety (non-patented in the United States). The parentage of the new variety can be summarized as follows:

'Just Joey'×('Meirestif'×'Meinarval').

The seeds resulting from the above pollination were sown and 98 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a substantially continuous basis light orange blossoms,
(b) is well suited for growing as attractive ornamentation in the landscape, and
(c) exhibits very good disease resistance.

The new variety well meets the needs of the horticultural industry and is particularly well suited for use as an ornamental planting in the landscape.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meibrinpay' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelii* understock and growing outdoors at Le Cannet des Maures, Var, France.

DETAILED DESCRIPTION

Figures 1, 2, 3, 4, 5, 6, 7, 8, 9, 10, 11, 12, 13, 14, 15:
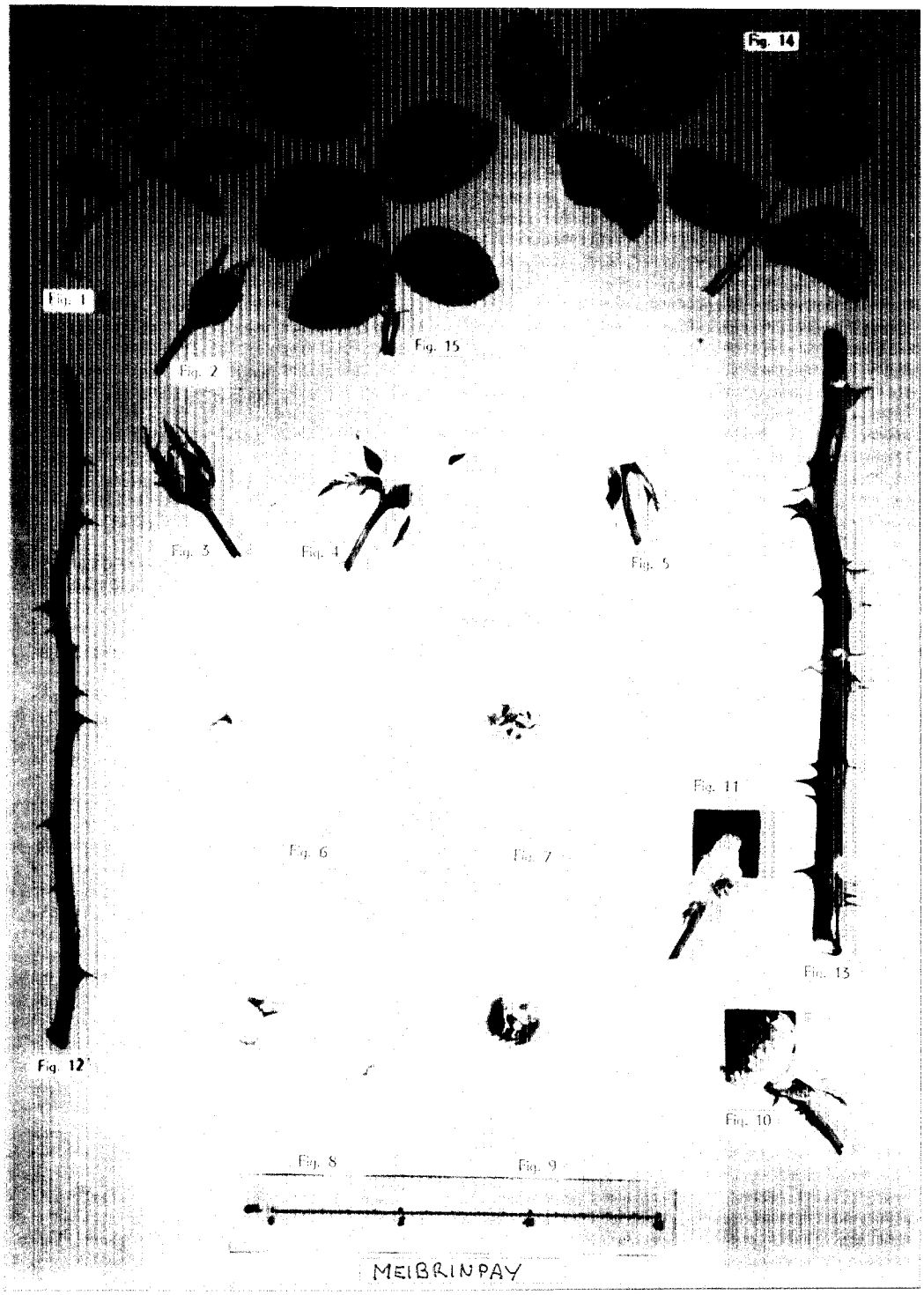
FIG. 1 illustrates a specimen of a young shoot.
FIG. 2 illustrates a specimen of a floral bud before any substantial opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of two leaves with three leaflets each—plan view—under surface (left) and upper surface (right)
FIG. 15 illustrates a speciment of a leaf with five leaflets—plan view—upper surface.

The chart used in the identification of the colors is that of The Royal Horiticultural Society (R.H.S. Colour Chart). The description is based on the observation of two year-old plants while budded on *Rosa froebelii* understock and growing outdoors at Le Cannet des Maures, Var, France. The coloration in common terms precedes reference to the chart.

Class: Hybrid Tea.

Plant:

*Height.*—Approximately 80 to 90 cm. on average at the end of the growing season. The stem length commonly is approximately 30 cm. on average.

*Habit.*—Narrow and bushy.

Branches:

*Color.*—Young stems: light green, Green Group 143C. Adult wood: medium green, Yellow-Green Group 146C.

*Thorns.*—Size: large. Quantity: numerous. Color: reddish on young stems and pinkish and greenish on adult wood.

Leaves:

*Stipules.*—Adnate, pectinate, large and linear.

*Petioles.*—Upper surface: striped reddish on young foliage and medium green on adult foliage with more or less glandular edges. Under surface: light green with a few prickles.

*Leaflets.*—Number: commonly 3 and 5. Shape: elliptic. Serration: single and regular. Texture: coriaceous. General appearance: dense. Color (young foliage): Upper surface: Lettuce Green, Yellow-Green Group 144A widely suffused with reddish coloration. Under surface: Lettuce Green, Yellow-Green Group 144A and widely suffused with reddish coloration. Color (adult foliage): Upper surface: dark green, Yellow-Green Group 147A. Under surface: light green, Green Group 137C.

Inflorescence:

*Number of flowers.*—Usually one per stem, and sometimes up to about 3 per stem. The flower productivity generally is average and approximates that of a typical hybrid tea rose variety.

*Peduncle.*—Light green and widely tinted with reddish brown. The length is approximately 3 cm. on average.

*Sepals.*—Upper surface: tomentose and light green on the inner surface and medium green on the outer surface. Under surface: medium green in coloration and commonly with a few extensions.

*Buds.*—Shape: egg-shaped. Length: approximately 3 to 3.5 cm. on average. Size: medium. Color upon opening: Upper surface: Cadmium Orange, Yellow-Orange Group 23C, and widely suffused with Apricot Orange, Orange Group 24C. Under surface: Orange on external petals and some Nasturtium Red, Orange-Red Group 32C on inner petals.

*Flower.*—Shape: cupped with a round center, and similar in configuration to old-fashioned roses. Diameter: approximately 10.5 cm. on average. Color (when opening begins): Upper surface: light orange, commonly ranging from Yellow-Orange Group 23C to Orange Group 24C with some fading or lightening with age on the outer petals. Color (when blooming): light orange commonly ranging from Yellow-Orange Group 23C to Orange Group 24C with some fading or lightening with age on the outer petals. Color (when blooming): light orange commonly ranging from Yellow-Orange Group 23C to Orange Group 24C with some fading or lightening with age on the outer petals. Under surface: light orange commonly ranging from Yellow-Orange Group 23C to Orange Group 24C with some fading or lightening with some fading or lightening with age on the outer petals. Color (at end of opening): Upper surface: light orange commonly ranging from Yellow-Orange Group 23C to Orange Group 24C with some fading or lightening with age on the outer petals. Under surface: light orange commonly ranging from Yellow-Orange Group 23C to Orange Group 24C with some fading or lightening with age on the outer petals. Fragrance: none. Lasting quality: very long. Petal number: approximately 25 to 31 on average. Petal shape: rounded. Lasting quality: the blossoms commonly last approximetely 5 to 7 days when cut and placed in a vase and approximately 7 to 9 days on the plant. The lives of such blossoms are greatly influenced by the season of the year and the environmental conditions that are encountered. Petal drop: good with the petals commonly becoming clearly detached when fully mature. Stamen number: approximately 188 to 195 on average. Anthers: normal ochre with a terminal insertion. Filaments: red-orange in coloration. Pistils: approximately 117 to 120 on average. Stigmas: yellowish in coloration. Styles: dark fuchsine in coloration, and more or less twisted. Receptacle: medium green, smooth, and in longitudinal section in the shape of a large pitcher. Hips: round-shaped hips and seeds commonly are formed.

Development:

*Vegetation.*—Strong.

*Blooming.*—Abundant and substantially continuous.

*Aptitude to bear fruit.*—Good.

*Resistance to diseases.*—Very good.

I claim:

1. A new and distinct variety of Hybrid Tea rose plant characterized by the following combination of characteristics:

(a) forms in abundance on a substantially continuous basis light orange blossoms, (b) is well suited for growing as attractive ornamentation in the landscape, and (c) exhibits very good disease resistance;

substantially as herein shown and described.

* * * * *

MEIBRINPAY